United States Patent [19]

Martin et al.

[11] Patent Number: 4,636,479

[45] Date of Patent: Jan. 13, 1987

[54] ENHANCED AGGLUTINATION METHOD AND KIT

[75] Inventors: Francis J. Martin, San Francisco; Viola T. Kung, Menlo Park, both of Calif.

[73] Assignee: Cooper-Lipotech, Inc., Menlo Park, Calif.

[21] Appl. No.: 486,793

[22] Filed: Apr. 20, 1983

[51] Int. Cl.[4] .................. G01N 33/546; G01N 33/555
[52] U.S. Cl. ................................... 436/533; 436/520; 436/534; 436/808; 436/819; 436/829
[58] Field of Search ................................ 436/506–509, 436/512, 539, 540, 808, 820, 829, 520, 533, 534, 808, 819, 829; 424/85; 435/4, 7; 252/316

[56] References Cited

U.S. PATENT DOCUMENTS 4,216,622 7/1980 Soothill et al. .............. 436/808
4,429,008 1/1984 Martin et al. ................ 436/829

FOREIGN PATENT DOCUMENTS 8301571 5/1983 European Pat. Off. ............ 436/829

OTHER PUBLICATIONS

Martin et al., "Inversible Coupling of Immunoglobulin Fragments to Profound Vervener", *J of Bio Chem,* vol. 257, 1/82, pp. 286–288.

*Primary Examiner*—Sidney Marantz
*Attorney, Agent, or Firm*—Ciotti & Murashige

[57] ABSTRACT

An enhanced agglutination assay method for determination of a multivalent analyte is disclosed. Analyte is added to agglutinatable particles coated with anti-analyte molecules to produce particle agglutination. The extent of agglutination is enhanced by mixing the particles and analyte with an analyte-binding reagent composed of lipid bodies. The reagent bodies act by promoting multiple analyte bridge connections between individual bridged particles and a reagent body. Also disclosed is a kit containing such particles and reagent.

24 Claims, No Drawings

ENHANCED AGGLUTINATION METHOD AND KIT

BACKGROUND AND SUMMARY

The following publications are referred to by corresponding number in this application:
1. Hupfer, B., Ringsdorf, H., and Schupp, H., Makromol. Chem. 182:247–253 (1981).
2. Regen, S.L., Czech, B., and Singh, A., J. Am. Chem. Soc., 102:6640–6641 (1980).
3. Szoka, F. Jr., and Papahadjopoulos, D., Ann. Rev. Biophys. Bioeng., 9:467–508 (1980).
4. Szoka, F., Jr. and Papahajopoulos, D., Proc. Nat. Acad. Sci. USA, 75:4194–4198 (1978).
5. Heath, T. D., Macher, B. A. and Papahadjopoulos, D., Biochimic et Biophysica Acta, 640:66–81 (1981).
6. Martin, F. J., Hubbell, W. L., and Papahadjopoulos, D., Biochemistry, 20:4229–4238 (1981).
7. Martin, F. J. and Papahadjopoulos, D., J. Biol. Chem., 257:286–288 (1982).
8. Carlsson, J., et al., Biochem. J. 173:723–737 (1978).
9. Curman, B., Klareskog, L., and Peterson, P. A., J. Biol. Chem., 255:7820–7826 (1980).
10. Smith, B. A. and McConnell, H. M., Proc. Nat. Acad. Sci. USA, 75:2759–2763 (1978).
11. Lowry, O. H., Rosebrough, N. J., Farr, A. L., and Randall, R. J., J. Biol. Chem., 193:265–275 (1951).

The present invention relates to an enhanced particle-agglutination assay method, and a kit for practicing such method.

A variety of methods for determining the presence or concentration of biochemical analytes is available. The analyte to be assayed typically is one which plays an important role in biochemical processes, or is diagnostic of a particular disease state, blood type, or the like.

Several important analyte assay techniques are based on specific, high affinity binding between the analyte to be assayed and an anti-analyte contained in an analyte assay reagent. The analyte and anti-analyte are opposite members of a high-affinity binding pair, which may include antigen-antibody, immunoglobulin-protein A, carbohydrate-lectin, transport protein-receptor protein, biotin-avidin, hormone-hormone receptor protein, and complementary oligo- and polynucleotide strand pairs. The terms "ligand" and "anti-ligand" will also be used herein to designate the opposite binding members in such a binding pair.

One general type of assay procedure which is based on specific ligand/anti-ligand binding involves the agglutination of particles to form visible clumps. The agglutinatable particles are coated with ligand molecules and mixed with multivalent, anti-ligand molecules to produce visible particle clumping, or aggregation. The multivalent, anti-ligand molecules function by bridging the ligands carried on different particles. Accordingly, the anti-ligand molecules must have at least two ligand binding sites which are arranged spatially to promote bridging between ligands on two different particles. The anti-ligand may be either divalent, meaning it has two such binding sites, or multivalent, meaning that more than two sites are present in the molecule. The term "multivalent" will be used herein to denote anti-ligand molecules containing two or more binding sites capable of bridging ligands carried on separate agglutinatable particles.

The analyte which is to be determined in a particle-agglutination test may be a cell-specific surface antigen (the ligand) carried on a biological cell (the agglutinatable particle). The addition of a known, multivalent anti-antigen reagent to the cells produces cell agglutination, evidencing the presence of such cell-specific surface antigens. In another general class of particle-agglutination tests, the analyte is the multivalent, anti-ligand which acts to produce agglutination of a ligand-coated particle assay reagent. Typically, in the latter type of agglutination test, the analyte is a serological component, such as an immunoglobulin or a multivalent antigen, and the agglutinatable particles are ligand-coated red blood cells or polymeric beads, such as latex particles.

A particle-agglutination test is performed routinely by mixing a suspension of ligand-coated agglutinatable particles with multivalent anti-ligand molecules in a small reaction volume. After a defined reaction period, which may be as short as a few minutes, the extent of particle agglutination is determined, usually by visual inspection. Particle-agglutination tests are thus relatively easy to perform, and the results are interpretable without sophisticated equipment. Additionally, typical particle-agglutination assay kits can be produced at a relatively low cost.

Despite these advantages, sensitivity limitations associated with prior art agglutination test methods have prevented application of the method to many analytes. One aspect of the sensitivity limitation is that visible particle agglutination may not be produced at analyte concentrations which one wishes to measure. Another aspect is that the time required for completion of the agglutination reaction, and the extent of agglutination produced (percentage of particles agglutinated) may make the test overly time consuming and difficult to interpret, respectively.

One object of the present invention, therefore, is to provide a particle-agglutination assay method in which assay sensitivity is substantially enhanced.

More particularly, it is an object of the invention to provide such an assay method which can be used to detect an analyte at a concentration which is substantially lower than that detectable according to particle-agglutination methods known in the prior art.

Another object of the invention is to provide such a method which can be used to produce a high percentage of strong, easily interpretable positive assay results, often in less time than that required by prior art particle-agglutination methods.

A specific object of the invention is to provide an improved agglutination assay methods for determination of rheumatoid factor and anti-nuclear antibody.

Another specific object of the invention is to provide an improved agglutination assay method for determination of hepatitis B surface antigen.

Yet another object of the invention is to provide an particle-agglutination assay kit for use in practicing the enhanced particle agglutination assay method of the invention.

A related object is to provide such a kit which is relatively inexpensive to produce.

The present invention includes an enhanced agglutination assay method for determination of a multivalent analyte. In the method, agglutinatable particles having surface-bound anti-analyte molecules are mixed with multivalent analyte molecules in a reaction medium to produce particle agglutination. The extent of agglutination produced by such mixing is enhanced by the addition of a reagent composed of analyte-binding bodies. Each reagent body is capable of bridging the particles by means of multiple analyte-molecule bridge connections between each of the bridged particles and the reagent body. A reagent composed of lipid bodies, each having a laterally mobile surface array of at least about 15 analyte-binding molecules per body, is advantageous in its ability to promote such multiple analyte-molecule linkages, even at relatively low surface concentrations of analyte-binding molecules on the reagent bodies.

The invention also contemplates a particle-agglutination assay kit which is usable in practicing the method of the invention. The kit includes agglutinatable particles adapted to combine with, and be crosslinked by the multivalent analyte which is to be determined. An analyte-binding reagent in the kit is adapted to enhance the extent of particle agglutination produced by the analyte alone.

These and other objects and features of the present invention will become more fully apparent from the following detailed description of the invention.

DETAILED DESCRIPTION OF THE INVENTION

According to one aspect of the invention, there is provided an enhanced particle agglutination assay method for determination of a multivalent analyte. In the method, a suspension of agglutinatable particles having surface-bound, anti-analyte molecules is mixed with analyte in a reaction medium to produce particle agglutination. The extent of agglutination so produced is enhanced, according to the invention, by adding to the reaction medium a reagent composed of analyte-binding bodies, each of which is capable of bridging such particles by means of multiple analytemolecule bridges connecting each of the bridged particles to the bridging reagent body. Such bridging is promoted particularly by a reagent composed of lipid bodies, each having a surface array of laterally mobile analyte-binding molecules. Details of the invention will be described below with particular reference to methods for producing the agglutinatable particles and the analyte-binding reagent, and to assay procedures used in practicing the invention.

Producing Agglutinatable Particles

As used herein, the term "agglutinatable particles" is intended to encompass water-insoluble particles which can be suspended in an aqueous medium and which, when aggregated or agglutinated into small clumps, can be distinguished readily from single, unagglutinated particles. Commonly, the clumps of agglutinated, or aggregated particles are distinguished from unagglutinated particles visually, according to one of a number of widely used visual-determination procedures which are described below. It is also contemplated herein that the agglutinated clumps may be distinguished from unagglutinated particles by physical separation techniques, such as differential centrifugation or filtration, according to difference in particle size and/or mass.

Two preferred types of particles which will be described herein are macromolecular beads and biological cells. Macromolecular beads may be formed of glass, cellulose, agarose, polystyrene, latex or the like. The beads are typically spherical particles, having particle sizes ranging between about 1 and 20 microns in diameter. The particles may be selected for, or chemically modified to have, a desired surface charge at the ionic strength and pH conditions at which the agglutination assay test is to be performed, or at which the particles are to be stored. Methods for attaching charged groups to the surface of macromolecular beads, including both glass and polymeric beads, are known to those skilled in the art.

The anti-analyte molecules which are attached to the macromolecular-bead particle include those which are capable of binding specifically and with high affinity to one or more binding sites in the multivalent analyte to be assayed. Among the analyte/anti-analyte binding pairs contemplated by the present invention are antigen-antibody, immunoglobulin-protein A, carbohydrate-lectin, biotin-avidin, hormone-hormone receptor protein, transport protein-receptor protein, and complementary nucleotide strands, where the anti-analyte may be either member of a pair. More generally, the anti-analyte may include any fragment or portion of an anti-analyte molecule which is capable of binding specifically and with high affinity to at least one of the analyte binding sites. For example, in an antibody-antigen pair, the anti-analyte antibody may include either antigen-binding $F(ab')_2$ or Fab' fragments. As another example, in the immunoglobulin-protein A pair, the anti-analyte immunoglobulin may include only the Fc immunoglobulin fragment.

The ligand molecules may be adsorbed to macromolecular-bead particles, or may be covalently attached thereto by a suitable coupling reaction. Where appropriate, the surface of molecular-bead particles are modified to contain a reactive group used in such covalent coupling. To illustrate, glass beads are modified to contain surface thio functions by derivatizing the beads with a glycerol-propylsilane reagent, activating with carbonyldiimidazole and converting into amino-glass by reaction with excess diamino alkane. The amino-glass is converted into pyridyl dithio glass by reaction with N-succinimidyl 3-(2 pyridyldithio) propionate. The pyridyl dithio glass in then reduced with dithiothreitol or 2-mercaptoethanol to yield particles whose surfaces have thio functions. Macromolecular beads, such as latex particles, having reactive surface groups, such as carboxylate or amino groups, are also commercially available. Methods for attaching ligand molecules to macromolecular beads, either by adsorption or covalent coupling, are well known in the art.

The agglutinatable particles may also include biological cells or cell-derived particles, such as cell membrane ghosts. Typical cells include various types of blood cells, particularly red blood cells. Also contemplated are virus particles, bacterial cells, and various plant and animal tissue cells which can be prepared as a suspension of dissociated cells by standard cell-culture procedures.

Where possible, cells containing endogenous cell-surface molecules specifically recognized by the multivalent analyte to be assayed are used. More commonly, anti-analyte molecules are attached to the cellular particles, according to known procedures, to produce a cell particle reagent coated with exogenous ligand molecules. Attachment of anti-analyte molecules to cell surfaces may be accomplished by adsorption, immunospecific bindings, or covalent coupling, similar to that described above with reference to macromolecular-bead particles. The surfaces of biological-cell particles can be modified by a variety of well known reactions, and the ionic strength of the cell-particle medium can be adjusted, to produce a desired cell surface charge.

Preparation of the Analyte-Binding Reagent

The analyte-binding reagent used in the invention to enhance particle agglutination preferably includes lipid bodies, each of which includes a lipid structure and an array of laterally mobile analyte-binding molecules carried on the surface of this structure. The lipid structure may take the form of closed unilamellar or multilamellar bilayer vesicles encapsulating an aqueous interior region, such vesicles also being referred to as liposomes. Amorphous lipid bilayer structures, including ribbon-like bodies and small aggregations of vesicles, or flocculants are also contemplated. Another possible lipid structure is formed by encapsulating an emulsified oil droplet with a lipid monolayer, such as a phospholipid monolayer. The stability of such a structure might be increased by partially polymerizing the monolayer components, according to lipid-monolayer polymerization reactions described, for example, in the above references 1 and 2.

According to one preferred method of forming reagent lipid bodies, there are first formed lipid bilayer vesicles. Analyte-binding molecules are then reacted with, or incorporated into the vesicle surfaces to produce vesicular reagent bodies. Non-vesicular lipid bodies, such as the ribbon-like and flocculant structures mentioned above, are produced by physically disrupting the vesicular bodies, for example, by freezing and thawing.

Properties of and methods for preparing lipid bilayer vesicles have been detailed in the literature. The reader is referred particularly to above references 3 and 4, and references cited therein, for a comprehensive discussion of the topic. What will be described herein are preferred methods of preparing lipid vesicles used in forming the reagent used in the invention, and vesicle properties which contribute to advantages in the invention.

Lipid vesicles are prepared from lipid mixtures which typically include phospholipids and sterols. A list of phospholipids used commonly in liposome preparations is given on page 471 of reference 3. One consideration which determines the choice of lipids used is the degree of fluid mobility and lipid packing density which is desired in the vesicles formed. As reported in a number of literature reports, these characteristics can be varied according to the lengths and degree of saturation of the aliphatic chains in the lipids, and the ratio of sterol to aliphatic chain lipids used. The significance of surface fluid mobility in the analyte-binding reagent used in the invention will be seen below. Packing density characteristics are important to the success of reactions used to attach analyte-binding molecules covalently to the vesicle surfaces. For example, it has been found that the inclusion of at least about 10% mole per cent of cholesterol is important for the success of certain protein-coupling reactions which will be described below. The fluidity and packing characteristics also affect the number of bilayers in the vesicles produced, and vesicle size.

The lipid composition is also selected to produce a requisite number of specific lipid head groups through which analyte-binding molecules can be coupled to the vesicle surfaces. The head groups, or necessary modifications thereof, may be formed after vesicles are prepared, or may be formed in the lipids before their incorporation into vesicles. Examples of lipids used in preferred coupling reactions will be discussed below.

The number and type of polar lipid groups may also be selected to produce a desired charge distribution on the lipid vesicles at a selected pH and ionic strength. The charge distribution may influence the coupling reaction used to attach analyte-binding molecules to the vesicles, and may be important in reducing non-specific aggregation of the reagent bodies and non-specific binding of the reagent bodies to agglutinatable particles. As will be seen below, it is generally desired to provide more highly negatively charged reagent bodies for use in conjunction with relatively uncharged agglutinatable particles, and less negatively charged reagent bodies for use with particles having a greater negative surface charge.

A typical lipid composition used in preparing lipid vesicles for use in the invention preferably includes between about 10 and 50% cholesterol or other sterol, between about 2 and 50% of glycolipid or phospholipid to which the enzyme and ligand molecules of the reagent can be individually coupled, with the remainder lipid composed of a neutral phospholipid, such as phosphatidylcholine, or a phospholipid mixture. Charged lipids, such as phosphatidylglycerol, phosphatidylserine, phosphatidic acid, glycolipids and charged cholesterol derivatives such as cholesterol phosphate or cholesterol sulfate may be included to produce a desired surface charge in the lipid vesicles.

Lipid vesicles may be formed by one of a variety of methods discussed particularly in reference 3. Multilamellar vesicles—that is, vesicles composed of a series of closely packed bilayer lamellae—can be prepared by drying a mixture of lipids in a thin film and hydrating the lipids with an aqueous buffer. The size and number of lamellae in the formed lipid vesicles can be controlled, within limits, by varying the hydration time and amount of agitation used in hydrating the lipids. Vigorous agitation, brief sonication or extrusion through polycarbonate membranes can be employed to obtain smaller and more uniformly sized multilamellar vesicles. However, it is generally desirable to use large vesicles in preparing the reagent used in the method of the invention.

In one preferred method of preparing large unilamellar vesicles, referred to as reverse phase evaporation, a desired composition of lipids is dissolved in a suitable organic solvent such as diethyl ether, isopropyl ether, or a solvent mixture such as isopropyl ether and chloroform (1:1). An aqueous solution is added directly to between about 3 and 6 volumes of the lipid-solvent mixture and the preparation is sonicated for a brief period to form a homogeneous emulsion. The organic solvent, or solvent mixture is removed under reduced pressure, resulting in the formation of a viscous, gel-like intermediate phase which spontaneously forms a vesicle dispersion when residual solvent is removed by evaporation under reduced pressure. The size of the resulting vesicles may be varied according to the amount of cholesterol included in the lipid mixture. The reader is referred to references 3 or 4 for further details concerning the reverse phase evaporation technique.

The reverse phase evaporation technique may be used to encapsulate water soluble molecules efficiently within the interior vesicle spaces. This feature is advantageous in the present invention where it is desired to encapsulate a water-soluble dye or the like within the vesicles, to enhance the visibility of agglutinated clumps containing the lipid bodies. The visibility of the lipid bodies used in the method of the invention can also be enhanced by attaching visible dye or fluorescent molecules to the lipid vesicles surfaces, according to well-known techniques.

The lipid vesicles prepared may be obtained in a defined size range by various techniques. Methods for reducing size heterogeneity in small unilamellar vesicles by gel filtration and ultracentrifugation have been described. A method of reducing the size and the size heterogeneity of lipid vesicles by extrusion through polycarbonate filters having selected pore sizes is described in reference 4.

It can be appreciated from the foregoing that lipid vesicles having a desired size range, shell thickness, fluid mobility and surface charge and reactivity characteristics may be prepared by proper selection of lipid components and preparative techniques. In addition, the prepared vesicles can be disrupted by physical disruption techniques to produce more amorphous lipid bodies, as will be seen.

The lipid bodies in the lipid reagent are prepared by forming on the surface of each vesicle, an array of laterally mobile analyte-binding molecules. The analyte-binding molecules are adapted to bind specifically and with high affinity to the multivalent analyte molecules to be assayed. That is, the analyte-binding and analyte molecules are opposite members of a binding pair of the type described above. Similar to what has been described above, the analyte-binding/analyte pair may include antigen-antibody, immunoglobulin-protein A, carbohydrate-lectin, biotin-avidin, hormone-hormone receptor protein, transport protein-receptor protein and complementary nucleotide strands. More generally, the reagent analyte-binding molecules may include any fragment or portion of a binding-pair molecule which is capable of participating with the analyte molecule in specific, high affinity binding. The analyte-binding molecules may include either member of the binding pair, consistent with the limitation that each analyte molecule must also include a second binding pair region capable of binding specifically to a particle anti-analyte molecule, and the analyte-binding molecules must be incapable of binding specifically and with high affinity to the particle anti-analyte molecules, under the reaction conditions used in the method of the invention. The analyte-binding molecules are preferably binding proteins, such as antibodies, protein A, and lectin, having epitope-specific binding groups that recognize and bind to epitopic sites on the analytes.

Several methods are available for coupling analyte binding molecules covalently to the polar head groups of vesicle lipids. As a general consideration, it is important to select a coupling reaction which does not significantly reduce the specific binding activity of the molecules being coupled. At the same time it is advantageous to select a method which produces a relatively high coupling efficiency. Finally, care must be exercised to avoid reactions which would produce significant cross linking of the vesicle lipid components to each other, or of the individually coupled analyte-binding molecules to one another, since any cross linking of the reagent components (except for the individual lipid/analyte-binding molecule conjugations) would reduce the fluid mobility of the surface lipids and attached molecules. Without intending to limit the scope of the invention, two preferred methods of coupling protein analyte-binding molecules to lipid vesicles will be described herein.

The first method involves Schiff-base formation between an aldehyde group on the lipid or molecule to be coupled, and a primary amino group on the other of the two reactants. The aldehyde group is preferably formed by periodate oxidation. The coupling reaction, after removal of the oxidant, is carried out in the presence of a reducing agent. Although the analyte-binding protein molecules may be oxidized, more commonly it is the lipid component which is the aldehyde precursor, since periodate treatment inactivates many proteins. Typical aldehyde-lipid precursors include lactosylceramide, trihexosylceramide, galactocerebroside, phosphatidylglycerol, phosphatidylinositol and gangliosides.

In practice, the vesicles are oxidized by periodate for a period sufficient to produce oxidation of a majority of the oxidizable lipid groups, and thereafter the vesicles are separated from the periodate by column gel filtration. Aldehyde groups on the vesicle surfaces are conjugated with a primary amine, such as a lysine group in a protein, to form a Schiff's base which is subsequently reduced with sodium borohydride or sodium cyanoborohydride to form a more stable bond. Typically, for conjugation reduced with sodium borohydride, oxidized lipid vesicles at a concentration of between about 5 and 10 micromoles (umoles) of total lipid are mixed in 1 ml with 10 to 30 milligrams (mg) of protein at an alkaline pH. The reaction is carried out for about 2 hours at room temperature. For conjugation reduced with sodium cyanoborohydride, the reaction typically is carried out over longer reaction times. The reader is referred to reference 5 for additional details.

Using lipid vesicles prepared by reverse phase evaporation and extruded through a 0.2 micron pore-size polycarbonate membrane, up to about 200 micrograms (ug) of immunoglobulin G (IgG) per u of lipid vesicle lipid can be attached to the vesicle surfaces by the above method. Based on a calculated number of about $1.2 \times 10^{12}$ vesicles per u of vesicle lipid, this conjugation ratio corresponds to about 600 IgG molecules per lipid vesicle. Correspondingly smaller molecules can be coupled to lipid vesicles in correspondingly larger numbers. Thus, up to about 1800 Fab' antibody fragments per lipid vesicle (in the 0.2 micron diameter range) can be attached. The method has wide applicability, due to the general availability of primary amine groups in proteins and other biomolecules which can be reacted with oxidation-produced aldehydes in selected lipids.

A second general coupling technique is applicable to thiol-containing molecules, involving formation of a disulfide or thioether bond between a vesicle lipid and the molecule attached. The technique is particularly useful for coupling F(ab')$_2$ and Fab' antibody fragments to lipid vesicles.

In the disulfide interchange reaction, phosphatidylethanolamine is modified to provide a pyridyldithio derivative which can react with an exposed thiol group in a protein or other type of biomolecule. The reader is referred to reference 6 for a detailed discussion of reaction conditions used in the method. As reported there, a coupling ratio of up to 600 u of Fab' antibody fragments per micromole of phospholipid can be achieved. Based on calculations similar to those presented above, this number corresponds to about 6000 Fab' antibody molecules per 0.2 micron diameter vesicle.

The thioether coupling method, which is described in detail in reference 7, is carried out by incorporating in the lipid vesicles a small proportion of a sulfhydryl-reactive phospholipid derivative, such as N-(4 (p- maleimidophenyl) butyryl) phosphatidylethanolamine (MPB-PE). The lipid vesicles are reacted with a thiol-containing protein to form an essentially irreversible thioether coupling between the protein thiol group and the MPB-PE maleimide group. It is noted that the requisite protein thiol group may be endogenous to the protein or may be introduced on the protein by amino-reactive thiol reagents according to known methods such as reported in reference 8. Coupling rations of up to about 350 mg of sulfydryl-containing protein per umole of lipid vesicle phospholipid have been obtained.

It is also contemplated herein that analyte-binding molecules can be attached to lipid vesicles by first coupling the molecules covalently to free lipids dispersed in a detergent solution. The lipid/analyte-binding molecule couples are then incorporated into lipid vesicles, either during vesicle formation or by diffusion into preformed vesicles according to known techniques.

Alternatively, the analyte-coupling molecule itself may contain an endogenous hydrophobic region —for example, a lipid group or a hydrophobic stretch of amino acids—by which the ligand can be incorporated into the surface of a lipid vesicle. As an example, it has been shown that human transplantation antigens can be attached to egg lecithin vesicles by anchoring hydrophobic peptide regions in the antigens to the vesicles (reference 9).

Reaction conditions used to couple molecules to the lipid vesicle surfaces (or incorporate molecules into the vesicle surfaces) are selected to produce a desired surface concentration of the analyte-binding molecules. Generally, the desired concentration is that which just produces an optimum, or near optimum particle agglutination enhancement in an agglutination assay method of the invention. Studies conducted in support of the present application show that the degree of particle agglutination enhancement produced by the lipid vesicle reagent described herein increases from a minimum surface concentration of about 15 molecules per lipid body, to a maximum of about 200 molecules per body (for vesicles of average diameter between about 0.2 and 0.4 microns). For proteins of about 50,000 dalton molecular weight, such as Fab' fragment molecules, and for vesicles in the 0.2 micron diameter size range, 15 to 200 molecules per vesicle corresponds roughly to between about 1.5 to 20 ug protein per umole vesicle lipid.

Little improvement in the ability of the reagent to enhance particle agglutination is seen above about 200 molecules per body. Cost of the reagent molecules becomes an important consideration, obviously, at higher surface concentrations of the reagent molecules.

As noted above, reactions capable of coupling an average of up to 6,000 molecules (in the 50,000 dalton molecular weight range) to a lipid vesicle (in the 0.2 micron diameter size range) are available. For relatively pure analyte-binding molecules, such as purified serum antibodies, monoclonal antibodies and purified antigens, the final surface concentration of molecules coupled to the lipid bodies may thus be a small fraction (e.g., less than 1%) of the achievable surface concentration. Conversely, a mixture of proteins containing, e.g., less than 1% specific analyte-binding proteins can be coupled to the vesicles at a concentration sufficient to produce the requisite 15-200 molecule per lipid body concentration of analyte-binding molecules. This feature is advantageous, for example, where the analyte-binding molecules used in forming the lipid reagent are contained in a serum-derived antibody or antibody fragment preparation which may contain as little as about 0.5% antibody or antibody fragment molecules specific against the selected analyte. By way of example, attachment of 3,000 molecules of an Fab' fragment preparation, containing 0.5% analyte-binding Fab' fragments, to lipid vesicles produces a concentration of analyte-binding Fab' fragments of about 150 molecules per vesicle (in the 0.2 micron diameter size range). Assuming that as many as half of the coupled molecules are inactivated by the coupling reaction, the reagent will still contain an average surface concentration of analyte-binding molecules of at least about 75 molecules per vesicle.

After the coupling reaction has been completed, the reagent vesicles may be physically disrupted, e.g. by freezing and thawing, to produce larger and more amorphous lipid bodies. Microscopic examination of a lipid vesicle reagent subject to one or more freezing and thawing steps showed a large percentage of lipid bodies having nonvesicular, ribbon-like structures, as well as flocculants, or small aggregations of lipid vesicles. Larger and/or more amorphous lipid bodies show a greater capacity to enhance particle agglutination in some particle agglutination tests (Example IV) but apparently not in others (Examples VII and VIII).

The freezing method is additionally useful in that the reagent, once frozen, can be stored over long periods without significant change in the ability of the reagent to enhance particle agglutination. The reagent vesicles may also be prepared for storage by lyophilization. Typically, a preparation of reagent lipid vesicles suspended in a dilute buffer is lyophilyzed conventionally and stored under vacuum conditions. For relatively short-duration storage, the lipid body reagent can be stored in solution, preferably at a temperature of between about 0° and 4° C. A storage solution containing a suspension of lipid bodies is preferably deoxygenated to minimize lipid-oxidation damage to the lipid body components.

The lipid body reagent may, under some circumstances, be mixed and stored with the agglutinatable particles prior to use in a particle-agglutination assay test. In accordance with one aspect of the invention, latex particles coated with anti-analyte molecules and reagent lipid bodies may be stored together as a stable, non-agglutinating cosuspension in a solution which also contains non-analyte proteins which act to minimize binding between the reagent lipid bodies and particles. Such a cosuspension is essentially as stable on storage as are the individual components in suspension.

In this regard, it is noted that the reagent analyte-binding molecules are generally incapable of binding directly to the particle anti-analyte molecules. However, for some analyte/anti-analyte pairs, the reagent analyte-binding molecules may crossreact weakly with the particle anti-analyte molecules in the absence of non-analyte molecules which are effective in preventing such binding. Where direct, weak reagent particle binding does occur, it is necessary to include such non-analyte molecules in the agglutination test reaction medium. In Example VI below, for example, it will be seen that non-analyte-containing serum is effective in preventing agglutination of IgG-coated latex particles by a lipid reagent containing anti-IgM analyte-binding molecules.

Properties of the analyte-binding reagent which are important in the assay method of the invention will now be considered. As noted above, enhanced particle agglutination requires a minimum average surface concentration of at least about 15 analyte-binding molecules per lipid body, with greater particle agglutination enhancement being observed as the average surface concentration of analyte binding molecules is increased up to about 200 molecules per lipid body. This finding is consistent with a mechanism of reagent action which involves the formation of multiple analyte-molecule bridge connections between each bridged particle and a bridging reagent body. If the reagent functioned by forming single analyte-molecule bridges between itself and the bridged particles, agglutination enhancement might be expected to occur at lower surface concentrations of analyte-binding molecules. In fact, it might be expected that a reagent having a relatively high surface concentration of analyte-binding molecules, by removing analyte molecules from solution, would actually be less effective in enhancing agglutination than a low-concentration reagent. This is not observed, apparently because multiple analyte molecules bound to a reagent are also bound to the particles, forming multiple bridge connections therebetween.

The ability of the reagent lipid bodies to promote particle agglutination through multiple analyte bridge connections may require that the reagent analyte-binding molecules be highly mobile, or fluid, at least at the 15 to 200 molecule per lipid body surface concentrations noted above. Diffusion constants on the order of $10^{-11}$ to $10^{-8}$ cm$^2$/sec for phospholipid diffusion within lipid bilayers have been measured (reference 10). The rapid diffusion would facilitate the formation of multiple analyte molecule bridge connections between a lipid body and each bridged particle by allowing several analyte-binding molecules to move to "bridge-forming" positions within a short time following an initial bridging event involving a single analyte molecule.

The nature of the interaction between reagent bodies and agglutinatable particles in the enhanced agglutination method was further examined by studies on the ability of polymeric-bead particles coated with analyte-binding molecules to enhance particle agglutination. In the studies, two latex-bead reagents were prepared, one formed with latex beads of mean diameter of about 3 microns, and one with latex beads of about 0.4 micron mean diameter.

Polybead-carboxylate monodispersed latex microspheres having one of the two mean diameters just noted, were purchased from Polysciences, Inc. To prepare the latex-bead reagent, 2 ml of 2.5% latex beads were conjugated with 2 mg of rabbit anti-human IgM F(ab')$_2$ antibody fragments obtained as in Example II below. The latex bead and antibody fragment components were reacted in the presence of 1-ethyl-3-(dimethylaminopropyl) carbodiimide hydrochloride (ECDI) overnight at room temperature. About 65% of the antibody fragment molecules were coupled to the latex beads in the reaction. Both the latex bead reagent formed with 3 micron-diameter beads and the one formed with 0.4 micron diameter beads were calculated to have a concentration of active, surface-accessible anti-IgM Fab' fragments in the 50-200 molecule per particle range, based on a particle size of 0.4 micron diameter. A suspension of the beads was agglutinatable directly by addition of human IgM molecules, indicating that anti-IgM Fab' fragment molecules on the bead surfaces were immunoreactive with solution analyte.

Each of the latex-bead reagents was tested for its ability to enhance the agglutination of three different commercially available rheumatoid factor (RF)-latex particles in the presence of RF+ serum, using materials and assay procedures described in Examples III and IV below. Each reagent was tested over a wide range of concentrations. In none of the tests did either of the latex-bead reagents produce any measurable particle agglutination enhancement of the RF-latex particles, unlike that observed for the lipid body reagents used in Examples III and IV.

The reagent latex particles have a sufficient surface concentration of analyte-binding proteins to form analyte-molecule bridge connections with other latex particles, as evidenced by the agglutination of the particles with IgM. It is presumed, therefore, that the inability of the latex particle reagent to enhance particle agglutination is due to its inability to form multiple analyte molecule bridge connections with partially agglutinated particles, and that this inability is related to the lack of lateral mobility of the analyte-binding proteins on the latex particle surfaces. As will be seen in Example IX below, bacterial particles coated with analyte-binding molecules are also incapable of enhancing particle agglutination according to the method of the invention.

Assay Procedures

According to one procedure used in practicing the invention, agglutinatable particles are first mixed with a multivalent analyte, and the two components are incubated for a selected period before the addition of analyte-binding reagent. This procedure has general applicability in practicing the method of the invention. Alternatively, in some applications, it is possible to add the analyte to a cosuspension of premixed particles and reagent lipid bodies. This procedure has obvious advantages in terms of the ease and simplicity of the assay test procedure, and a kit based on this method may be somewhat less expensive since the particles and lipid reagent can be supplied in a single mix.

The assay reaction is carried out in a suitable reaction medium which may include a biological specimen fluid, such as a serological sample, containing the multivalent analyte to be assayed. The pH of the reaction medium is one which is compatible with ligand/anti-ligand binding reactions, and preferably between about 5 and 9. More specifically, the pH and/or ionic strength of the reaction medium may be adjusted to achieve a desired charge interaction between the agglutinatable particles and the reagent lipid bodies. As a general rule, it is advantageous to perform the agglutination reaction at an ionic strength and pH which produces moderate charge repulsion between the particles and reagent lipid bodies in the reaction. In the absence of such charge repulsion, the particles may be aggregated nonspecifically by the lipid bodies, producing a false positive. On the other hand, if the charge repulsion between the particles and lipid bodies is too great, the agglutination reaction may be suppressed, resulting in poor test sensitivity.

Experimentally, it has been found that with red blood cell agglutinatable particles, optimum agglutination enhancement is observed when the reaction is performed under conditions where the red blood cells carry a slight negative charge and where the reagent lipid bodies are prepared to contain between about 10 and 20 mole percent of negatively charged lipid components. With substantially uncharged polymeric-bead particles, such as latex particles, best results are observed, under similar pH and ionic strength conditions, with reagent lipid bodies having between about 20 and 50 mole percent by negatively charged lipid components.

The degree of agglutination enhancement observed in the method of the invention is dependent on the relative concentrations of the three reaction components—the agglutinatable particles, the analyte molecules, and the analyte-binding reagent. The concentration of reagent bodies required to produce optimal agglutination enhancement typically is less for reagent bodies having higher analyte-binding molecule surface concentrations.

The ratio of components in such an assay test can be optimized by mixing a standard concentration of agglutinable particles with one of a series of dilutions of multivalent analyte to determine the limit of sensitivity of particle agglutination in the absence of the lipid body reagent.

Serial dilutions of analyte-binding reagent are added to the aliquots of particles and threshold amounts of analyte. The extent of agglutination observed in each sample is scored, usually qualitatively in terms of of a 1+ to 4+ grade scale (described below). Concentrations of analyte-binding reagent bodies which produce enhanced agglutination in the method of the invention typically fall within the range between about 10 micromolar (uM) and 1 millimolar (mM).

In one typical protocol used in practicing the method of the invention, the reaction components are mixed in a small reaction volume, typically between about 50 and 100 microliters (ul), on a glass microscope slide. After addition of the analyte-binding reagent for a suitable reaction period, the extent of agglutination is determined by visual inspection of the drop, preferably using light microscopy. In several of the examples described below, the extent of particle agglutination is characterized by a 1+, 2+, 3+ or 4+ grade, according to the following definitions: 1+, up to 25%; 2+, 25% to 50%; 3+, 50% to 75%; and 4+, 75% to 100% particle agglutination.

The agglutination reaction of the method of the invention can also be performed in a small-volume centrifuge tube in which the agglutinatable particles may be pelleted by centrifugation following the agglutination reaction. In a typical protocol, agglutinatable particles are reacted with an analyte sample and the lipid body reagent under suitable reaction conditions. The reaction tube is then centrifuged, for example at 1,000 times G for one minute, to pellet the agglutinatable particles and the reaction components associated therewith. The analyte-binding reagent bodies remain suspended in the reaction medium under the centrifugation conditions employed.

The extent of agglutination in the pelleted particles is determined, qualitatively, by agitating the sample in a manner which produces a resuspending of the particles into the reaction medium supernatant. It can be appreciated that agglutinated particles will separate from the particle pellet in characteristic clump-like bodies upon resuspension, while unagglutinated particles will disperse more evenly into the reaction supernatant. The initial resuspension event may be followed by a relatively rapid settling of the larger agglutinated-particle clumps, wherein the extent of agglutination can be gauged visually by the degree of cloudiness or color which is imparted to the reaction medium by the resuspended particles. This test protocol is used more frequently to determine agglutination of blood cell particles.

In a third reaction procedure, the reaction components are mixed in a micro-titer well. As the particles settle, they form a pattern in the bottom of the well which is distinctive either of agglutinated or non-agglutinated particles. This test procedure is used particularly with biological cell particles, such as red blood cells.

Considering now various advantageous features of the invention, the method of the invention provides a significant improvement in test sensitivity over prior art agglutination-test methods. One aspect of the improved sensitivity is the increased extent of agglutination produced at a given level of analyte. As will be seen in Examples III-IX below, the method of the invention characteristically enhances the extent of agglutination observed in commercial assay kits 2- to 3-fold, at relatively low analyte concentrations.

Another aspect of the increased sensitivity is the capability of detecting levels of analyte which are sub-threshold in prior art agglutination tests. Analyte sample which give 1-grade agglutination or less (i.e., sub-threshold) agglutination in standard agglutination tests using macromolecular-bead or red blood cell particles are also referred to herein as weakly positive analyte samples. As will be seen in Examples VII and VIII, a 2- to 4-fold increase in the limit of analyte detectability may be achieved in the present invention, with respect to prior art particle-agglutination methods.

The method of the invention can, in some agglutination tests, reduce particle agglutination time. In the assay test for rheumatoid factor (RF) detailed in Example V below, the time required for completion of the enhanced agglutination test was less than half that required for the prior art test reaction.

Another aspect of the invention which can be appreciated from the above is the provision of an improved agglutination assay kit for determination of a multivalent analyte. The kit includes, in addition to particles adapted to be agglutinated by analyte molecules, a reagent composed of analyte-binding lipid bodies, each of which is capable of bridging such particles by multiple analyte-molecule bridge connections between each reagent body and a bridged particle. Because of the relatively large number of surface molecules which can be included in the lipid bodies, and the relatively low number of analyte-binding molecules required for producing enhanced agglutination, the source of the analyte-binding molecules used in preparing the reagent can be a relatively impure preparation containing as little as about 0.5 mole percent of analyte-binding molecules. Examples I and II below describe methods for preparing lipid body reagents using unfractionated antibody fragments.

The particle and reagent components in the kit may be provided in a form suitable for long-term storage. In fact, in some cases, freezing the reagent lipid bodies for storage produces a physical disruption of the bodies which increases the ability of the reagent to enhance particle agglutination. This feature is discussed particularly in Example IV below.

The particle and reagent component in the test may, in some cases, be supplied together as a cosuspension whose use in an assay test involves merely addition of an analyte to be assayed. Examples VI and IX below describe stable storage mixtures of latex beads and reagent lipid particles.

The following examples describe particular embodiments of making and using the invention.

EXAMPLE I

Preparation of Lipid Vesicles

Lipid vesicles formed from lipids containing either 0, 10 or 20 mole percent of phosphatidylglycerol (PG), were prepared. The vesicles included, in addition to PG, phosphatidylcholine (PC), cholesterol, and MPB-PE, a negatively charged, sulfhydryl-reactive phospholipid used in coupling analyte-binding molecules to the vesicles. The molar ratios of the lipid components in the three vesicle preparations are shown in TABLE I. The values in TABLE I indicate the umole quantities of each lipid component which were used in forming each vesicle preparation. The mole percent of negatively charged phospholipid components in each of the vesicle preparations is the sum of the PG and MPB-PE components, i.e., either 10, 20 or 30 mole percent of total phospholipids.

The lipid components were dissolved in 1 ml diethyl ether. To each lipid sample, 325 ul of a buffer containing 10 mM NaPO$_4$, 10 mM NaCL, 2 mM EDTA at pH 6.0, was added, and the two phases emulsified by sonication for one minute at 25° in a bath sonicator. Ether was removed from the emulsion under reduced pressure at room temperature to produce the lipid vesicles.

TABLE I

|        | PC | PG | MPB-PE | Chol. |
|--------|----|----|--------|-------|
| 0% PG  | 9  | 0  | 1      | 10    |
| 10% PG | 8  | 1  | 1      | 10    |
| 20% PG | 7  | 2  | 1      | 10    |

Each of the lipid vesicle preparations was examined by light microscopy. The lipid structures were almost exclusively vesicular in nature and most of the vesicles were in the 0.1 to 10.0 micron diameter range and had one or a few bilayer lamella.

EXAMPLE II

Preparation of Anti-Human IgM Lipid Body Reagent

A purified preparation of rabbit antibodies, containing an estimated 1% to 3% of rabbit anti-human IgM antibodies, was obtained conventionally. F(ab')$_2$ dimers were prepared by pepsin digestion of the antibody preparation. The dimer fragments were reduced with dithiothreitol at a pH of about 4.8 to produce Fab' monomer fragments. The pH of the reduction reaction is important in that when the reaction is performed significantly above pH 4.8 (i.e., pH 5.0) overreduction may occur which leads to inactivation of the antibody fragments, while underreduction, which may occur at a lower pH (i.e., pH 4.5), is characterized by relatively poor coupling efficiency of the vesicles. The Fab' monomer sample showed a single band when analyzed by sodium dodecyl sulfate polyacrylamide gel electrophoresis (SDS-PAGE), indicating a substantially homogenous preparation containing wholly reduced monomers with no contaminants.

For each lipid vesicle preparation, 1 umole of the lipid vesicles which had been extruded through a 0.4 micron filter was reacted with freshly prepared Fab' fragments at one of the protein concentrations between 0.6 and 1.4 mg per ml indicated in Table II. The coupling reaction was carried out overnight at room temperature in 10 mM NaPO$_4$, 10 mM NaCl and 2 mM EDTA, at pH 6.8. After the conjugation reaction, the liposomes were freed of unbound protein by pelleting at 17,000 rpms for 40 minutes. The pelleted reagent samples were resuspended in low salt buffer at 4° C. to a final concentration of 1 umole per ml.

The protein concentration of the reagent samples was determined according to the method described in reference 11. The protein concentration in each of the 15 reagent samples prepared is shown in Table II, expressed in terms of ug Fab' per umole vesicle lipid. The approximate average number of Fab' molecules coupled to each vesicle (in the 0.4 micron diameter range) can be calculated by multiplying the protein concentration values shown in Table II by 40. Thus, the sample prepared by reacting lipid vesicles containing 0% PG with 0.6 mg per ml Fab' contains an average of about 4,800 Fab' molecules per vesicle. Assuming that about 1% of the total number of Fab' molecules in the reagent are anti-human IgM antibody fragments, and of these, up to about half have been inactivated by the coupling reaction, it can be seen that this sample contains about 24 active anti-human IgM molecules per vesicle. Likewise, the sample prepared by reacting vesicles containing 10 mole percent PG with 1.4 mg per ml protein, producing the highest protein-concentration sample, contains about 116 active anti-human IgM molecules per vesicle.

TABLE II

|        | 0.6 | 0.8 | 1.0 | 1.2 | 1.4 mg/ml          |
|--------|-----|-----|-----|-----|--------------------|
| 0% PG  | 120 | 225 | 253 | 293 | 342 μg Fab'/       |
| 10% PG | 123 | 210 | 268 | 378 | 580 μmole lipid    |
| 20% PG | 135 | 209 | 286 | 358 | 465                |

EXAMPLE III

Evaluation of Reagent Samples in a Latex Agglutination Test System

The 15 anti-IgM reagent samples prepared in accordance with Example II were studied for their ability to enhance particle agglutination in commercially available rheumatoid factor (RF) agglutination tests. RF refers to a diverse group of immunoglobulins in the IgM class often found in patients with rheumatoid arthritis. The IgM analyte is capable of binding specifically to IgG (carried on the agglutinatable particles) and is recognized specifically by anti-IgM antibodies (in the lipid body reagent).

Rheumatoid factor (RF)- agglutination test kits, were obtained from Helena Laboratories, Beaumont, TX and from Organon Diagnostics, West Orange, NJ. The latex reagent from each of the commercial sources was incubated with an RF+ test serum at 37° C. for 15 minutes. The amount of test serum used was that which produced about a 1+ agglutination reaction on the 4-grade scale described above, when incubated with the latex particles alone. After the initial incubation, increasing concentrations of each of the 15 different anti-IgM reagent samples prepared in accordance with Example II was added to its reaction mixture, and the mixture was agitated for another 30 minutes at 37° C. Each tube was centrifuged at 1,000 × G for one minute and examined visually for agglutination.

The following results were noted: Reagent samples containing 20 mole percent PG (30 mole percent negatively charged lipids) produced the strongest agglutination enhancement, with the samples containing 0% PG producing almost no observable agglutination enhancement. Samples containing protein concentrations higher than about 250 ug protein per umole phospholipid (about 50 molecules of active anti-IgM molecules per lipid vesicle of diameter of about 0.4 micron) produced stronger agglutination enhancement than the samples having lower protein concentrations. The best reagent samples tested produced an agglutination enhancement in the Helena test kit from about 1+ to 2+ or 3+, and in the Organon test kit, from about 2+ to 3+. That is, the addition of the reagent produced an approximately 2- to 3-fold increase in the number of particles agglutinated in the test, at a given analyte concentration.

EXAMPLE IV

The Effect of Reagent Lipid Body Size and Morphology on Particle Agglutination Enhancement An RF-latex particle preparation (lot 002) consisting of latex particles coated with human IgG molecules was obtained from Cooper Diagnostics, Inc., Palo Alto, CA. Lipid vesicles containing 20% PG were prepared according to the procedure in Example I, and coupled to rabbit anti-human IgM Fab' fragments, at a final protein concentration of around 260 ug protein per umole phospholipid, according to the method of Example II. The lipid vesicle reagent was then subjected to physical disruption by freezing and thawing and/or sizing by passage through a defined-size, polycarbonate micropore filter, as indicated in Table III. The reagent bodies which were subject to a freeze-thaw cycle were examined by light microscopy and found to include a large percentage of ribbon-like, non-vesicular lipid structures, and amorphous, flocculant lipid bodies, as well as vesicular bodies. Passage of reagent bodies through membranes having the pore sizes in microns (um) indicated in Table III produced lipid bodies whose largest diameters were approximately the size of the membrane pores.

In each assay test, 2 ul of the lipid body reagent indicated in the table were mixed with 20 ul of the RF-latex reagent and 20 ul of RF+ serum for two minutes on a glass slide. The extent of agglutination was characterized according to the 4-grade scale described above. The grade 1- in TABLE III indicates slight, detectable clumping which is substantially less than the 1+ level agglutination.

TABLE III

| Reagent added | Agglutination Grade |
| --- | --- |
| none | 1− |
| frozen, non-extruded | 4+ |
| frozen, extruded by 1.0 μm membrane | 2+ |
| frozen, extruded by 0.8 μm membrane | 1+ |
| frozen, extruded by 0.6 μm membrane | 1+ |
| non-frozen, non-extruded | 3+ |
| non-frozen, extruded by 1.0 μm membrane | 1+−2+ |
| non-frozen, extruded by 0.8 μm membrane | 1+ |
| non-frozen, extruded by 0.6 μm membrane | 1+ |

As seen from the data in the table, each lipid body reagent used enhanced the extent of agglutination over that observed with particles alone. Reagent lipid bodies which had been frozen and not sized by passage through defined-pore membranes produced the most striking increase in the extent of the agglutination observed. Comparison of the data obtained for the other lipid body reagents suggests that lipid bodies disrupted by freezing and thawing are more effective than comparable-size vesicular bodies, and that larger lipid bodies are more effective than smaller, comparable-structure lipid bodies in producing agglutination enhancement.

EXAMPLE V

Enhanced Particle Agglutination Assay to Detect Rheumatoid Factor

The ability of an IgM-binding lipid body reagent to enhance the agglutination observable in an RF-particle agglutination assay test was examined. The agglutinatable particles were the RF-latex particles from Cooper Diagnostics, Inc. used in the experiment reported in Example IV. The RF-binding reagent used was that produced according to Example IV. The reagent bodies were physically disrupted by freezing and thawing and were unmodified in size. Eleven serum samples, including one RF− and ten RF+ samples, were tested.

In each test, 20 ul of latex particles, 20 ul of a 20-fold diluted serum sample and 2 ul of lipid body reagent were incubated in a drop on a glass slide for two minutes. The drops were then immediately examined for agglutination, and graded 1+ to 4+. The results are shown in Table IV below. As in Example IV, the grade designation 1- indicates a very slight agglutination which is substantially less than about 25% agglutination.

TABLE IV

| Sample | − reagent | + reagent |
| --- | --- | --- |
| 1 | — | — |
| 2 | 1− | 1− |
| 3 | 1− | 1− |
| 4 | 1− | 1+ |
| 5 | 1+ | 1+ |
| 6 | 1+ | 3+ |
| 7 | 2+ | 3+ |
| 8 | 2+ | 3+ |
| 9 | 3+ | 4+ |
| 10 | 3+ | 4+ |
| 11 | 4+ | 4+ |

As seen from the data, the addition of the lipid body reagent did not change the reading observed for the RF− serum of sample 1, nor inhibit the extent of agglutination for the stongly positive RF+ sample 11. For the other nine samples, which were graded between 1− and 3+ in the absence of reagent, six were enhanced 1 or 2 grades in agglutination by the addition of the lipid body reagent.

The data above indicate that an important advantage of the enhanced agglutination method of the invention is the improved readability of a test, due to a greater percentage of strong positives (3+, 4+) which are produced. To examine this feature further, 71 sample sera, including 30 drawn from "normal" blood donors and 41 drawn from patients known to have rheumatoid arthritis were tested by the enhanced agglutination method just described. Of the 30 samples from normal blood donors, 29 were negative and one was positive (1+) by the enhanced agglutination test. Of the 42 samples from rheumatoid arthritis patients, 11 were negative, 4 were 2+ or less and 27 were 3+ or more. Thus, out of the total of 31 samples which gave a positive reading, 27 gave a strongly positive, easily readable 3+ or 4+ reading. The readability of the test, in terms of the percentage of 3+ or 4+ reactions observed, was substantially better than that obtained in parallel tests with commercially available RF-latex kits. Moreover, the time required to produce maximum agglutination in an enhanced agglutination test was less than half the time required for full agglutination to develop in commercially available RF-latex assay kits.

EXAMPLE VI

Storage of Particles and Reagent Lipid Bodies as a Cosuspension

This example demonstrates that the particle and reagent components of a kit designed for use in practicing the present invention may be stored together as a cosuspension and used as a single reagent. The particle and reagent components used were RF-latex particles (lot 003) obtained from Cooper Diagnostics, Inc., Palo Alto, CA and the anti-IgM lipid body reagent used in Examples IV and V above, respectively.

When the particles and lipid body reagent were sorted together, in the absence of serum sample, some particle agglutination was observed, possibly due to cross reactivity of rabbit anti-human IgM carried on the lipid bodies with altered human IgG carried on the latex particles. This agglutination was avoided by adding a small amount of $RF^-$ serum to the particle lipid reagent mixture. Experimentally, 100 ul of latex particles, 100 ul of diluted $RF^-$ serum (22 ug per ml) and 10 ul (30 nmole) of the lipid body reagent were mixed and stored overnight at 4° C. In an enhanced agglutination assay test, 50 ul of the particle/reagent mixture was mixed with 50 ul of pre-diluted $RF^+$ serum and incubated for periods ranging from one to four minutes. The results were compared with the agglutination produced by adding 50 ul of $RF^+$ serum to an equal volume of latex particles alone (diluted to the particle concentration in the particle/reagent mixture). The extent of agglutination produced by mixing the particle/reagent mixture with an equal volume of $RF^-$ serum was also determined.

TABLE V

|  | 1 min. | 2 min. | 3 min. | 4 min. |
|---|---|---|---|---|
| particle/reagent mixture + $RF^+$ | 1− | 2+ | 4+ | 4+ |
| particles + $RF^+$ | 1− | 1− | 1− | 1− |
| particle/reagent mixture + $RF^-$ | — | — | — | — |

A comparison of the first two rows of data in TABLE V demonstrate that the reagent mixture composed of agglutinatable particles and lipid body reagent provides a more than 3-grade enhancement (after 4 min.) of $RF^+$ particle agglutination over that in RF-latex particles alone. The third row of data shows that little or no particle agglutination occurs in the particle reagent mixture in the absence of $RF^+$ analyte.

EXAMPLE VII

Enhanced Latex Particle Agglutination Test to Detect Hepatitis B Surface Antigen Hepatitis B surface antigen (HBsAg) is a multivalent antigen found in the serum of patients with hepatitis. Three lipid body reagents adapted to bind to HBsAg were formed from vesicles having the three lipid compositions indicated in Table I. A blend of three monoclonal anti-HBsAg antibodies specific against "a" HBsAg subunit was thiolated with an 18-fold molar excess of M-succinimidyl 3-(3-pyridyldithio) propionate (SPDP) for 20 minutes at room temperature, according to the method reported in reference 9. The reaction produced an average degree of thiolation of about 4.6 SH groups per antibody molecule. The thiolated antibody was reduced with dithiothreitol at pH 4.5, prior to conjugation with the lipid vesicle preparations. Approximately half of the protein was lost as precipitate when the reaction medium was titrated to pH 4.5.

For each of the three vesicle preparations (containing 0, 10 or 20 mole percent PG) vesicles at a concentration of 1 umole lipid per ml were incubated with 1 mg per ml thiolated antibody in 10 mM $NaPO_4$, 10 mM NaCl and 2 mM EDTA at pH 6.8, at room temperature overnight. After completion of the conjugation reaction, the protein-coated lipid bodies were freed of unbound protein by pelleting at 17,000 rpm for 40 minutes. The amount of protein coupled to the vesicles ranged from a high of about 1.6 mg protein per umole vesicle phospholipid, for vesicles containing 0% PG, to about 1.2 mg protein per umole vesicle phospholipid, for vesicles containing 20% PG.

Latex beads obtained from Cooper Diagnostics, Inc., Palo Alto, CA, were sensitized with the above blend of the three monoclonal anti-HBsAg antibodies. The analytes tested were purified HBsAg, subtypes $adw_2$ and $ayw_3$. Initially, 20 ul of latex reagent was incubated with a test sample on a slide for 4 or 5 minutes, and then inspected visually for agglutination. The limit of HBsAg that can be detected by HBsAg-latex particles alone is approximately 30 ug per ml for subtype $adw_2$ and 20 ug per ml for subtype $ayw_3$. In a second series of tests, 20 ul of latex reagent was incubated with a test sample on a slide for 1 minute, and then a selected concentration of one of the three different lipid body reagents was added. The extent of agglutination was determined after an additional 4 minutes of incubation on the slide.

Each of the three lipid body reagents (containing either 0%, 10% or 20% PG) enhanced the limit-of-detection sensitivity about 4-fold for HBsAg, subtype $adw_2$ and about 2-fold for HBsAg, subtype $ayw_3$. That is, the limit of HBsAg that can be detected in the enhanced agglutination test was about 10 ug per ml for both HBsAg subtypes. The lipid body reagent enhanced the extent of agglutination observed about 2 grades over what was observed in the absence of the reagent at the same HBsAg concentration. The ability of the lipid body reagents used herein to enhance agglutination was not increased by subjecting the reagent to one or more freeze-thaw cycles.

EXAMPLE VIII

Enhanced Red Blood Cell Agglutination Test for the Determination of Hepatitis B Surface Antigen The three lipid body reagents of Example VII were also tested for their ability to enhance the agglutination of HBsAg-sensitized erythrocytes from a commercially available HBsAg erythrocyte agglutination test kit.

Erythrocytes sensitized with anti-HBsAg antibody (guinea pig), were obtained from Abbott Laboratories, North Chicago, IL. The analytes tested were the purified HBsAg subtypes $adw_2$ and $ayw_3$ used in Example VII. The enhanced agglutination reaction was performed by adding 2 ul of a selected concentration of one of the analyte specimens to 50 ul of a mixture of the sensitized erythrocytes and one of the lipid body reagents on a microtiter plate. After 1.5 hours, the plate was placed on top of a test reading mirror and the agglutination pattern determined conventionally.

The sensitivity of sensitized erythrocytes alone in an agglutination test for HBsAg was determined to be about 25 nanograms (ng) per ml for subtype $adw_2$ and about 160 ng per ml for the subtype $ayw_3$. With the addition of an anti-HBsAg lipid body reagent, and particularly the reagent containing 0% PG, both the sensitivity and readability of the test were significantly enhanced. The limit-of-detection sensitivity of HBsAg increased about 4-fold for subtype $adw_2$ and about 2-fold for $ayw_3$. That is, the enhanced agglutination test was capable of detecting HBsAg, subtype $adw_2$ at a level of about 6 ng per ml, and subtype $ayw_3$, at a level of about 80 ng per ml. At comparable concentrations of HBsAg analyte, the extent of agglutination was enhanced about 2 grades over that observed in the absence of the lipid body reagent. The lipid body reagent formed from lipid vesicles containing 0% PG showed a stronger agglutination enhancement than the lipid body reagents formed from 10% or 20% PG-containing vesicles. The enhancement in the sensitivity and readability of the test produced by co-incubating erythrocytes, analyte HBsAg, and lipid body reagent on a microtiter plate was about the same as that produced by the addition of lipid body reagent after preincubation of erythrocytes and analyte HBsAg.

EXAMPLE IX

Enhanced Latex Particle Agglutination to Detect Anti-Nuclear Antibody

Anti-nuclear antibody (ANA) encompasses a group of IgG-type antibodies which are immunoreactive with diverse nuclear antigens. The antibody is strongly correlated with connective tissue diseases such as rheumatoid arthritis and systemic schleroderma, and with the autoimmune disease lupus erythrematosus. The Fc portion of the antibody is bound strongly by protein A, a bacterial surface protein which also binds strongly to a variety of other immunoglobulins.

A lipid-body reagent containing a surface array of protein A was formed from vesicles having the lipid composition shown in Table I for the vesicles containing 10% PG. Protein A from Staphylococcus aureus was obtained from Sigma Chemical Co. (St. Louis, MO). The protein A binding capacity was about 12.5 mg human IgG per mg of protein. The protein was thiolated by reacting 5 mg of protein A with 200 ug of SPDP in a pH 7.5 buffer for 30 minutes at room temperature, according to the method reported in Reference 8. The unreacted SPDP was removed by Sephadex G-25 column chromatography. The reaction produced an average degree of thiolation of about 1 SH group per protein A molecule. The thiolated protein A was reduced with 20 mM dithiothreitol, pH 6.0, at room temperature for 20 minutes prior to conjugation with the lipid vesicle preparation.

The lipid body reagent was prepared by reacting 0.5 umole, of lipid vesicles with 0.4 mg thiolated protein A overnight at pH 6.6. After completion of the conjugation reaction, the protein A-containing lipid bodies were freed of unbound protein by pelleting at 17,000 rpm for 40 minutes. The amount of protein A coupled to the vesicles was about 100 ug protein per umole vesicle phospholipid.

ANA-latex beads composed of latex beads coated with calf thymus chromatin were obtained from Cooper Diagnostics, Inc., Palo Alto, CA (lot 003). A positive control ANA serum obtained from Travenol Lab, Inc., Hyland Diagnostics Div. (Deerfield, IL) was diluted 1:4 in saline. Staphylococcus aureus was obtained from Cal Biochem (LaJolla, CA) as a 10% w/v suspension. The suspension had a binding capacity of about 2 mg of human IgG per ml.

Initially, 50 ul of the 1:4 dilution serum was incubated with 50 ul of ANA-latex on a slide for 2 minutes, then inspected visually for agglutination. The extent of agglutination was graded at about 1+. An enhanced agglutination assay was performed by incubating 50 ul of the above serum with a mixture containing 50 ul ANA-latex plus 6 ul (18 nmole) of the lipid body reagent, under similar reaction conditions. The addition of the lipid reagent enhanced the extent of agglutination one grade to 2+. A 2-grade enhancement in the extent of latex agglutination was observed in a test where 50 ul of serum were mixed with a mixture containing 50 ul of latex particles plus 9 ul (27 nmole) of the lipid body reagent.

A lipid body reagent composed of lipid vesicles coated with anti-human IgG antibodies was also examined for its ability to enhance ANA-latex agglutination. The reagent, which was prepared substantially in accordance with the method described in Example II, produced no observable ANA-latex enhancement. The failure of the lipid body reagent containing anti-human IgG to enhance latex agglutination is likely due to neutralization of the reagent antibodies by the relatively large concentration of non-ANA immunoglobulin molecules contained in the 1:4 dilution serum used in the assay. It is not known why the lipid body reagent containing protein A was not similarly neutralized by serum IgG molecules. One explanation is that protein A combines more strongly with IgG molecules which are complexed with an immunospecific antigen than with unbound IgG.

The ability of S. aureus cells, which bear a coating of protein A on their surfaces, to enhance latex particle agglutination in the ANA test was also studied. The bacterial cells were killed according to known procedures, retaining a substantially rigid array of active protein A molecules on their surfaces. In one test, 50 ul of ANA-positive serum was mixed with 50 ul of latex plus various quantities of S. aureus cells which, at the highest cell levels, contributed a higher concentration of protein A in the reaction mixture than did 27 nmole of the protein A-containing lipid-body reagent. At none of the S. aureus cell concentrations was any latex-agglutination enhancement observed. The ability of the S. aureus cells to enhance agglutination in a two-step incubation assay method, in which the control serum was incubated with ANA-latex particles to produce agglutination prior to the addition of the S. aureus cells, was also studied. No increased agglutination was observed at any of the several cell concentrations added. Since S. aureus cells have about the same size as the reagent lipid bodies (about 1 micron diameter), and an adequate surface concentration of protein A, their inability to enhance agglutination is apparently due to the relatively non-mobile nature of the protein A molecules on the bacterial cell walls, preventing the cells from forming multiple analyte bridge connections with the latex particles.

An advantage of the protein A-containing lipid body reagent is that the reagent can also react specifically with a variety of other immunoglobulins, including human IgG of subclasses 1, 2 and 4 and with some subclasses of human IgA and IgM. The reagent can therefore be used to enhance agglutination in test kits for determination of several other immunoglobulin analytes.

The protein A-containing lipid body reagent is stable on storage with the ANA-latex particles. Thus the reagent and latex particles can be supplied and used as a single reagent suspension.

While the invention has been described with particular reference to specific examples, it will be understood that these examples are in no way intended to limit the scope of the invention. Various changes and modifications can be made without departing from the spirit of the invention.

What is claimed is:

1. An enhanced agglutination assay method for determination of a multivalent analyte in a weakly positive analyte-containing sample, said method comprising:
   providing an unagglutinated suspension of (a) agglutinatable particles between about 1 and 20 microns in diameter and having surface-bound anti-analyte molecules effective to produce particle agglutination in the presence of such analyte, and (b) liposomes having surface-bound analyte-binding protein molecules, at an average surface concentration of at least about 15 analyte-binding molecules per liposome, these molecules being effective to bind the analyte concurrently with analyte binding to a particle-bound anti-analyte molecule.
   adding such analyte-containing sample to the suspension, and
   by said adding, producing a degree of particle agglutination which is at least 1-2 grades greater, on a 1-4 grade scale, than that which would be produced by adding the anaylte sample to a suspension of the particles in the absence of the liposomes.

2. The method of claim 1, wherein the liposomes are added such that the resulting reaction medium has a final liposome concentration of between about 10 micromolar and 1 millimolar.

3. The method of claim 1, wherein the liposomes are composed of lipid-bilayer vesicles in the 0.4 to 10 micron diameter size range.

4. The method of claim 1, wherein the agglutinatable particles are latex particles.

5. The method of claim 1, wherein the analyte molecules include multivalent antigen molecules, and both the particle anti-analyte molecules and the analyte-binding molecules include anti-antigen antibody or antibody fragment molecules.

6. The method of claim 5, wherein the antigen includes hepatitis B surface antigen, and the antibody or antibody fragment molecules include anti-hepatitis B surface antigen antibodies.

7. The method of claim 1, wherein the analyte is an IgG, and the analyte-binding molecules, include protein A molecules.

8. The method of claim 7, wherein the analyte includes anti-nuclear antibody contained in a sample containing non-antigen specific immunoglobulins which are also recognized specifically by protein A.

9. The method of claim 1, wherein the analyte molecules include antibody molecules which bind immunospecifically to the particle anti-analyte molecules, and the analyte-binding molecules include binding proteins which bind specifically to the analyte antibody molecules.

10. The method of claim 9, wherein the analyte molecules include IgM molecules and the analyte-binding molecules include anti-IgM antibody or antibody fragment molecules covalently attached to the surface lipid components in the liposomes.

11. The method of claim 10, wherein the IgM molecules include rheumatoid factor.

12. An enhanced agglutination assay kit for determination of a multivalent analyte in a weakly positive analyte-containing sample, comprising:
    an unagglutinated suspension of (a) agglutinatable particles between about 1 to 20 microns in size, and having surface-bound anti-analyte molecules adapted to promote particle agglutination in the presence of the analyte, and (b) liposomes having surface-bound analyte-binding molecules, at an average concentration of at least about 15 analyte-binding molecules per liposome, these molecules being effective to bind the analyte concurrently with analyte binding to a particle-bound anti-analyte molecule.
    said liposomes being present in an amount effective to produce a degree of particle agglutination, when such analyte sample is added to the suspension, which is at least 1-2 grades greater, on a 1-4 grade scale, than that which would be produced by adding the analyte to a suspension of the particles in the absence of the liposomes.

13. The kit of claim 12, wherein the concentration of liposomes supplied is between about 20 micromolar and 1 millimolar in the reaction medium.

14. The kit of claim 12, wherein the liposomes are composed of lipid-bilayer vesicles in the 0.4 to 10 micron diameter size range.

15. The kit of claim 12, wherein the particles include polymeric beads, and the liposomes include more than about 20 mole percent of negatively charged lipid components.

16. The kit of claim 12 wherein the particles include red blood cells, and the liposomes include less than about 20 moles percent of negatively charged lipid components.

17. The kit of claim 12, wherein the agglutinatable particles are latex particles.

18. The kit of claim 12, wherein the suspension further includes ribbon-like lipid bilayer structures formed by freezing and thawing liposomes.

19. The kit of claim 12 for use in determination of an antibody analyte, wherein the particle anti-analyte molecules and the analyte-binding molecules include binding proteins adapted to bind specifically to the molecules of the analyte antibody.

20. The kit of claim 19 for use in determination of an IgM analyte such as rheumatoid factor, wherein the particle anti-analyte molecules include IgG molecules, and the analyte-binding molecules include anti-IgM antibody or antibody fragment molecules covalently attached to surface lipid components in the liposomes.

21. The kit of claim 12, for use in determination of a multivalent antigen, wherein both the particle anti-analyte molecules and analyte-binding molecules include anti-antigen antibody or antibody fragment molecules.

22. The kit of claim 11 for use in determination of hepatitis B surface antigen, wherein the antibody or antibody fragment molecules include anti-hepatitis B surface antigen antibodies.

23. The kit of claim 12, for use in determining an antigen-specific immunoglobulin which is recognized specifically by protein A and which is contained in a sample containing non-antigen-specific immunoglobulins which are recognized specifically by protein A, wherein the particles have surface-bound antigen molecules and the reagent analyte-binding molecules include protein A molecules.

24. The kit of claim 23, wherein the antigen includes anti-nuclear antibody.

* * * * *